(12) United States Patent
Bax et al.

(10) Patent No.: US 10,357,346 B2
(45) Date of Patent: Jul. 23, 2019

(54) ACTUATOR WITH ENHANCED MAGNETIC SPRING FUNCTION FOR PERSONAL CARE APPLIANCE

(71) Applicant: KONINKLIJKE PHILIPS N.V., Eindhoven (NL)

(72) Inventors: Pieter Johannes Bax, Drachten (NL); Franciscus Jozef Bosman, Drachten (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 326 days.

(21) Appl. No.: 15/108,590

(22) PCT Filed: Dec. 8, 2014

(86) PCT No.: PCT/IB2014/066680
§ 371 (c)(1),
(2) Date: Jun. 28, 2016

(87) PCT Pub. No.: WO2015/101851
PCT Pub. Date: Jul. 9, 2015

(65) Prior Publication Data
US 2016/0324610 A1    Nov. 10, 2016

Related U.S. Application Data

(60) Provisional application No. 61/921,675, filed on Dec. 30, 2013.

(51) Int. Cl.
*A61C 17/34* (2006.01)
*H02K 33/18* (2006.01)
(Continued)

(52) U.S. Cl.
CPC ............. *A61C 17/34* (2013.01); *A46B 9/04* (2013.01); *A61C 17/221* (2013.01);
(Continued)

(58) Field of Classification Search
CPC ......... A46B 9/04; A61C 17/221; A61C 17/34; A61C 17/3418; A61C 17/3445; A61C 17/3472; H02K 2201/18; H02K 33/18
(Continued)

(56) References Cited

U.S. PATENT DOCUMENTS

| 2009/0070948 A1 | 3/2009 | Bax |
| 2012/0001499 A1* | 1/2012 | Makino ................. H02K 41/03 310/12.14 |

(Continued)

FOREIGN PATENT DOCUMENTS

| EP | 1626483 A1 | 2/2006 |
| EP | 1684401 A1 | 7/2006 |

(Continued)

*Primary Examiner* — Alex W Mok (57) ABSTRACT

An actuator (52) for a personal care appliance (50) comprises a housing (54), a spindle (64), a tangential actuator portion (70), and an axial actuator portion (72). The tangential actuator portion (70) includes first and second magnet and pole assemblies (76,78) that define a tangential spring function of the tangential actuator portion. The axial actuator portion (72) includes third and fourth magnet and pole assemblies (90,92) that define an axial spring function of the axial actuator portion. At least one of (i) the first and second magnet and pole assemblies (76,78) of the tangential actuator portion (70) and (ii) third and fourth magnet and pole assemblies (90,92) of the axial actuator portion are configured to enhance a corresponding spring function of the axial actuator portion or tangential actuator portion, respectively.

15 Claims, 4 Drawing Sheets

(51) Int. Cl.
*A46B 9/04* (2006.01)
*A61C 17/22* (2006.01)

(52) U.S. Cl.
CPC ......... *A61C 17/3472* (2013.01); *H02K 33/18* (2013.01); *A61C 17/3418* (2013.01); *A61C 17/3445* (2013.01); *H02K 2201/18* (2013.01)

(58) Field of Classification Search
USPC .......................................................... 310/47
See application file for complete search history.

(56) References Cited

U.S. PATENT DOCUMENTS

| | | | |
|---|---|---|---|
| 2012/0043832 A1* | 2/2012 | Neff | ................... H02K 41/0356 310/12.14 |
| 2012/0262259 A1* | 10/2012 | Teo | ........................ H02K 16/00 335/296 |
| 2013/0207575 A1 | 8/2013 | Bax et al. | |

FOREIGN PATENT DOCUMENTS

| | | | |
|---|---|---|---|
| JP | 2004254411 A | 9/2004 |
| JP | 2013540412 A | 10/2013 |
| WO | 2004047670 A1 | 6/2004 |
| WO | 2007020599 A2 | 2/2007 |
| WO | 2012042427 A2 | 4/2012 |

* cited by examiner

ACTUATOR WITH ENHANCED MAGNETIC SPRING FUNCTION FOR PERSONAL CARE APPLIANCE

CROSS-REFERENCE TO PRIOR APPLICATIONS

This application is the U.S. National Phase application under 35 U.S.C. § 371 of International Application No. PCT/IB2014/066680, filed on Dec. 8, 2014, which claims the benefit of U.S. Provisional Patent Application No. 61/921,675, filed on Dec. 30, 2013. These applications are hereby incorporated by reference herein.

The present embodiments relate generally to drive systems for a personal care appliance, such as a power toothbrush, and more particularly, to a combined tangential and axial motion drive system with enhanced magnetic spring function.

Figure 1:
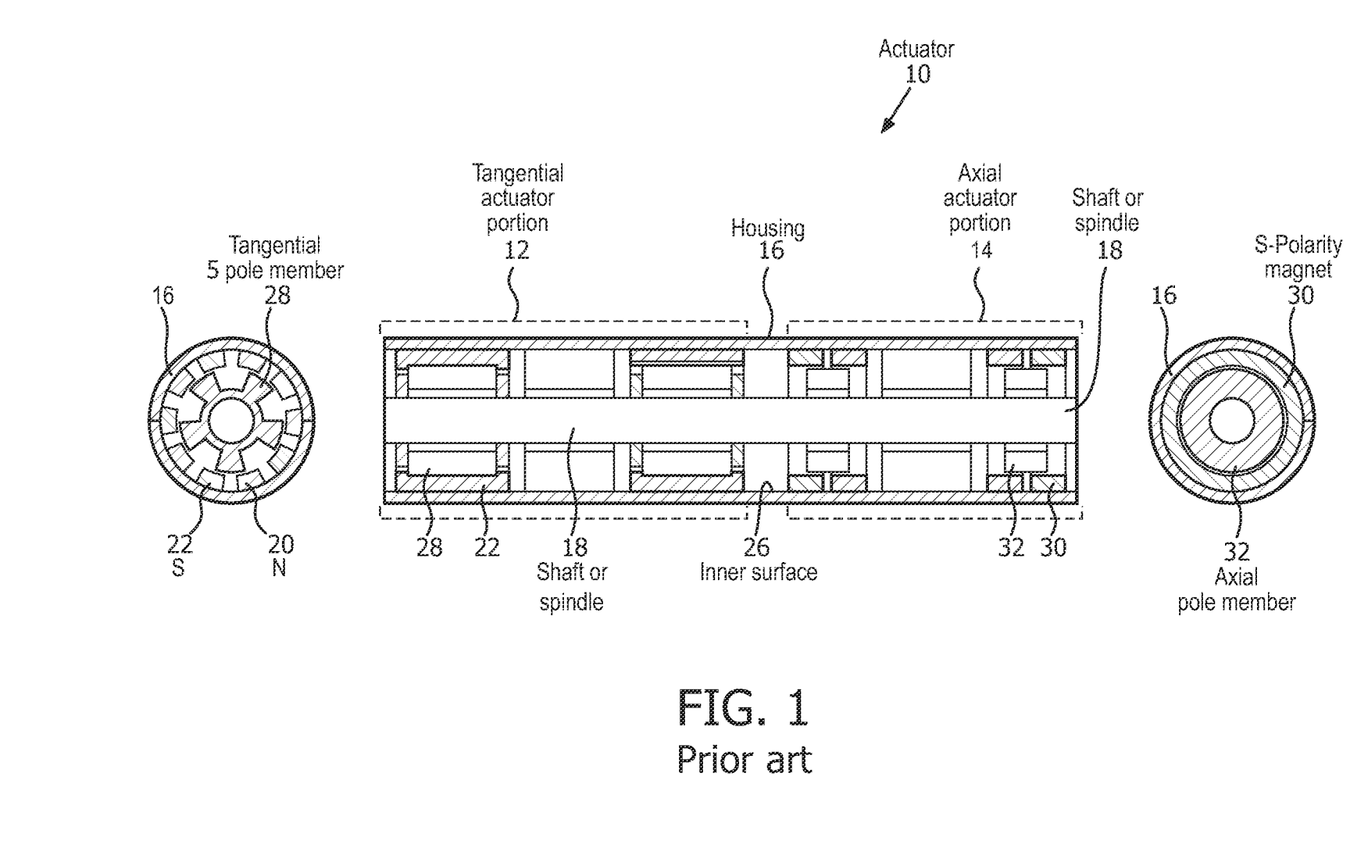
FIG. 1 is a cross-sectional view of an actuator having a tangential actuator portion and an axial actuator portion according to the prior art.

FIG. 1 is a cross-sectional view of a dual motion actuator 10 having a tangential actuator portion 12 and an axial actuator portion 14 according to the prior art. The tangential actuator portion 12 and the axial actuator portion 14 share the same housing 16 and shaft (or spindle) 18. The left-hand portion of FIG. 1 illustrates an end view of the actuator 10, and in particular, the tangential actuator portion 12, as seen from the left-hand end. The right-hand portion of FIG. 1 illustrates the other end view of the actuator 10, and in particular, the axial actuator portion, 14, as seen from the right-hand end.

The tangential actuator portion 12 generally comprises a resonant system in which a spring function is delivered by an electromagnetic system of (i) small magnets mounted on the inside of the cylindrical housing 16 and (ii) poles mounted on the shaft 18 within the cylindrical housing 16. Housing 16 comprises metal. The small magnets comprise N-polarity and S-polarity magnets, 20 and 22, respectively mounted on an inner surface 26 of the cylindrical housing 16. Each N-polarity magnet 20 and S-polarity magnet 22 is further longitudinally disposed on the inner radial surface 26 of the housing 16, that is, directed perpendicularly into the page of the left-hand end view of the left-hand portion of the drawing figure. The actuator poles (i.e., the actuator pole assembly) of the tangential actuator portion 12 comprise, for example, a 5-pole member such as indicated by reference numeral 28. The five (5) pole members of the pole assembly are of equal dimension and equally spaced apart in a radial configuration disposed about the spindle or shaft 18. In addition, a cogging position of the poles (i.e., rotor) has a spring characteristic when rotating the shaft.

In other words, with reference still to FIG. 1, the magnet and pole assembly of a portion of the tangential actuator portion 12 includes a plurality of N-polarity and S-polarity magnets indicated by reference numerals 20 and 22, respectively. The plurality of N-polarity and S-polarity magnets comprises ten (10) magnets of equal dimension, and equally spaced apart (i.e., an equi-gapped N magnet and S magnet arrangement), about an inner radial surface 26 of housing 16. Each N-polarity magnet 20 and S-polarity magnet 22 is further longitudinally disposed on the inner radial surface 18 of the housing 16. The magnet and pole assembly further includes a pole assembly 28 having five (5) pole members of equal dimension and equally spaced apart in a radial configuration disposed about the spindle or shaft 18. In this configuration, the prior art tangential actuator has one effective cogging position that provides a single tangential actuator characteristic.

Still further, the axial actuator portion 14 of FIG. 1 has evenly distributed north (N) and south (S) magnets and poles. The axial actuator portion 14 generally comprises full ring magnets (N and S) and a full disc cores. For example, as illustrated on the right-hand side of FIG. 1, an S-polarity ring magnet 30 of the axial actuator portion 14 is mounted on the inner surface of the housing 16 and an axial pole member 32 (i.e., a full disc core) is mounted on the shaft 18.

One disadvantage of the prior art actuator 10 of FIG. 1 is that both actuator portions are defined as independent actuators. A spring constant is achieved by a magnetic preference position of the rotor in two directions (i.e., axial and tangential). The axial system tends to be too stiff, and the tangential system stiffness too low, i.e., for use in a drive system for a personal care appliance. To achieve a required stiffness, relatively high magnet volume is needed. All of the stators are N or S alternating along the shaft length. In other words, to obtain a desired tangential stiffness requires too much magnet volume to reach the desired stiffness.

Accordingly, an improved method and apparatus for overcoming the problems in the art is desired.

In accordance with one aspect, an actuator for a personal care appliance is disclosed which includes a tangential actuator portion and an axial actuator portion in which the function of the two actuator portions is improved, without using an increased magnet volume. One actuator portion can advantageously contribute to the stiffness of the other actuator portion, and vice versa. According to the embodiments of the present disclosure, the geometry for both actuator portions, as disclosed herein, advantageously provides the mutual effect that the function of both actuator portions is improved. The improvement further allows for reducing a total required magnet volume, and thus reducing a cost of manufacture or production of actuator.

According to one embodiment, an actuator for a personal care appliance comprises a housing, a spindle, a tangential actuator portion, and an axial actuator portion. The tangential actuator portion includes first and second magnet and pole assemblies that define a tangential spring function of the tangential actuator portion. The axial actuator portion includes third and fourth magnet and pole assemblies that define an axial spring function of the axial actuator portion. At least one of (i) the first and second magnet and pole assemblies of the tangential actuator portion and (ii) third and fourth magnet and pole assemblies the axial actuator portion are configured to enhance a corresponding spring function of the axial actuator portion or tangential actuator portion, respectively.

The housing comprises magnetic material having an inner radial surface and a principal axis extending longitudinally along a length dimension thereof. The housing further includes at least first and second portions along the length dimension thereof. The spindle comprises magnetizable material extending longitudinally within the housing along the principal axis of the housing. The spindle further includes at least first and second portions corresponding with the at least first and second portions of the housing, respectively.

The tangential actuator portion is coupled between the first portion of the housing and the first portion of the spindle. The tangential actuator portion comprises (i) a first permanent magnet and pole assembly, (ii) a second permanent magnet and pole assembly, and (iii) an electromagnetic coil disposed about and coupled to the spindle in-between the first and second magnet and pole assemblies. In operation, responsive to a rotation control signal applied to the electromagnetic coil, the tangential actuator portion rotationally displaces the spindle with respect to the housing about the principal axis.

The axial actuator portion is coupled between the second portion of the housing and the second portion of the spindle, wherein the axial actuator portion comprises (i) a third permanent magnet and pole assembly, (ii) a fourth permanent magnet and pole assembly, and (iii) a second electromagnetic coil disposed about and coupled to the spindle in-between the third and fourth magnet and pole assemblies. In operation, responsive to a translation control signal applied to the second electromagnetic coil, the axial actuator portion axially displaces the spindle with respect to the housing along the principal axis.

In another embodiment, the actuator further comprises a controller for providing at least one selected from the group consisting of the rotation control signal, the translation control signal, and any combination of both rotation and translation control signals.

In a further embodiment, the axial actuator portion increases a tangential stiffness in the tangential spring function of the tangential actuator portion.

In another embodiment, the tangential actuator portion increases an axial stiffness in the axial spring function of the axial actuator portion.

In yet another embodiment, a complement of sub-pole members and magnet sub-segments of the axial actuator portion produces a spring function that enhances the tangential spring function of the tangential actuator portion of the actuator.

In another embodiment, the third permanent magnet and pole assembly of the axial actuator portion comprises (i)(a) a first longitudinally disposed sequence of magnet segments spaced apart according to a first longitudinal spacing pattern in a first longitudinal orientation and having a first polarity order of first (N) and second (S) magnetic polarities. Each segment of the first longitudinally disposed sequence of magnet segments is circumferentially disposed about the inner radial surface within the second portion of the housing. At least one segment of the first longitudinally disposed sequence of magnet segments comprises a ring of at least two sub-segments of a same polarity spaced apart from one another by a given radial spacing about a respective given circumference of the inner radial surface.

The third permanent magnet and pole assembly of the axial actuator portion comprises (i)(b) a third pole assembly having a least one pole member disposed about and on the second portion of the spindle for establishing an axial cogging relationship with the first longitudinally disposed sequence of magnet segments. The at least one segment of the first longitudinally disposed sequence of magnet segments further comprises at least two segments, wherein (i) a first one of the at least two segments comprises sub-segments of a first polarity spaced apart from one another by a given radial spacing about a respective given circumference of the inner radial surface and (ii) a second one of the at least two segments comprises sub-segments of a second polarity, opposite the first polarity, spaced apart from one another by a given radial spacing about a respective given circumference of the inner radial surface.

In yet another embodiment, (i) the first one of the at least two segments of the first longitudinally disposed sequence of magnet segments and (ii) the second one of the at least two segments of the first longitudinally disposed sequence of magnet segments (iii) comprise neighboring segments (i.e., longitudinally adjacent segments or segments adjacent to one another in a longitudinal direction).

In a further embodiment, the at least one pole member of the third pole assembly further comprises at least two sub-pole members arranged in a first radial configuration disposed about the spindle. The first radial configuration comprises the at least two sub-pole members being configured to complement the at least two sub-segments of the at least one segment of the first longitudinally disposed sequence of magnet segments. In another embodiment, the sub-pole members complement sub-segments by (i) a free-end radial surface of each sub-pole member of the third pole assembly extending radially outward towards an inner radial surface of a corresponding sub-segment of the at least one segment of the first longitudinally disposed sequence of magnet segments, proximate to, but separated by a gap from, the inner radial surface of the of a corresponding sub-segment, and (ii) a free-end radial dimension of each sub-pole member of the third pole assembly being approximately equal to an inner radial dimension of a corresponding sub-segment.

In a further embodiment, the fourth permanent magnet and pole assembly of the axial actuator portion comprises (ii)(a) a second longitudinally disposed sequence of magnet segments spaced apart according to a second longitudinal spacing pattern in a second longitudinal orientation and having a second polarity order of first (N) and second (S) magnetic polarities, opposite to the first polarity order of the first longitudinally disposed sequence of magnet segments of the third permanent magnet and pole assembly. Each segment of the second longitudinally disposed sequence of magnet segments is circumferentially disposed about the inner radial surface within the second portion of the housing. The fourth permanent magnet and pole assembly of the axial actuator portion further comprises (ii)(b) a fourth pole assembly having a least one pole member disposed about and on the second portion of the spindle for establishing an axial cogging relationship with the second longitudinally disposed sequence of magnet segments.

In a further embodiment, at least one segment of the second longitudinally disposed sequence of magnet segments comprises at least two sub-segments of a same polarity spaced apart from one another by a given radial spacing about a respective given circumference of the inner radial surface. The at least one segment of the second longitudinally disposed sequence of magnet segments further comprises at least two segments, wherein (i) a first one of the at least two segments comprises sub-segments of a first polarity spaced apart from one another by a given radial spacing about a respective given circumference of the inner radial surface and (ii) a second one of the at least two segments comprises sub-segments of a second polarity, opposite the first polarity, spaced apart from one another by a given radial spacing about a respective given circumference of the inner radial surface.

In a still further embodiment, (i) the first one of the at least two segments of the second longitudinally disposed sequence of magnet segments and (ii) the second one of the at least two segments of the second longitudinally disposed sequence of magnet segments (iii) comprise neighboring segments (i.e., longitudinally adjacent segments or segments adjacent to one another in a longitudinal direction).

In a still further embodiment, at least one pole member of the fourth pole assembly further comprises at least two sub-pole members arranged in a second radial configuration disposed about the spindle. The second radial configuration comprises the at least two sub-pole members being configured to complement the at least two sub-segments of the at least one segment of the second longitudinally disposed sequence of magnet segments. The sub-pole members complement sub-segments by (i) a free-end radial surface of each sub-pole member of the fourth pole assembly extending radially outward towards an inner radial surface of a corresponding sub-segment of the at least one segment of the second longitudinally disposed sequence of magnet segments, proximate to, but separated by a gap from, the inner radial surface of the of a corresponding sub-segment, and (ii) a free-end radial dimension of each sub-pole member of the fourth pole assembly being approximately equal to an inner radial dimension of a corresponding sub-segment.

A personal care appliance includes the actuator according to the embodiments disclosed herein, wherein the personal care appliance comprises one selected from the group consisting of an electric toothbrush, an oral hygiene device, a tooth polishing device, and any combination thereof.

In a still further embodiment, an actuator for a personal care appliance comprises:

(a) a cylindrical housing of magnetic material having an inner radial surface and a principal axis extending longitudinally along a length dimension thereof, the housing further including at least first and second portions along the length dimension thereof;

(b) a spindle of magnetizable material extending longitudinally within the housing along the principal axis of the housing, the spindle further including at least first and second portions corresponding with the at least first and second portions of the housing, respectively;

(c) a tangential actuator portion coupled between the first portion of the housing and the first portion of the spindle, wherein the tangential actuator portion comprises (i) a first permanent magnet and pole assembly, (ii) a second permanent magnet and pole assembly, and (iii) an electromagnetic coil disposed about and coupled to the spindle in-between the first and second magnet and pole assemblies, wherein responsive to a rotation control signal applied to the electromagnetic coil, the tangential actuator portion rotationally displaces the spindle with respect to the housing about the principal axis;

(d) an axial actuator portion coupled between the second portion of the housing and the second portion of the spindle, wherein the axial actuator portion comprises (i) a third permanent magnet and pole assembly, (ii) a fourth permanent magnet and pole assembly, and (iii) a second electromagnetic coil disposed about and coupled to the spindle in-between the third and fourth magnet and pole assemblies, wherein responsive to a translation control signal applied to the second electromagnetic coil, the axial actuator portion axially displaces the spindle with respect to the housing along the principal axis; and (e) a controller for providing at least one selected from the group consisting of the rotation control signal, the translation control signal, and any combination of both rotation and translation control signals.

The first and second magnet and pole assemblies define a tangential spring function of the tangential actuator portion, and the third and fourth magnet and pole assemblies define an axial spring function of the axial actuator portion, and at least one of (i) the first and second magnet and pole assemblies of the tangential actuator portion and (ii) third and fourth magnet and pole assemblies the axial actuator portion are configured to enhance a corresponding spring function of the axial actuator portion or tangential actuator portion, respectively.

The third permanent magnet and pole assembly of the axial actuator portion further comprises (i)(a) a first longitudinally disposed sequence of magnet segments spaced apart according to a first longitudinal spacing pattern in a first longitudinal orientation and having a first polarity order of first (N) and second (S) magnetic polarities, each segment of the first longitudinally disposed sequence of magnet segments being circumferentially disposed about the inner radial surface within the second portion of the housing, wherein at least one segment of the first longitudinally disposed sequence of magnet segments comprises at least two sub-segments of a same polarity spaced apart from one another by a given radial spacing about a respective given circumference of the inner radial surface, and (i)(b) a third pole assembly having a least one pole member disposed about and on the second portion of the spindle for establishing an axial cogging relationship with the first longitudinally disposed sequence of magnet segments.

The fourth permanent magnet and pole assembly of the axial actuator portion comprises (ii)(a) a second longitudinally disposed sequence of magnet segments spaced apart according to a second longitudinal spacing pattern in a second longitudinal orientation and having a second polarity order of first (N) and second (S) magnetic polarities, opposite to the first polarity order of the first longitudinally disposed sequence of magnet segments of the third permanent magnet and pole assembly, each segment of the second longitudinally disposed sequence of magnet segments being circumferentially disposed about the inner radial surface within the second portion of the housing, and (ii)(b) a fourth pole assembly having a least one pole member disposed about and on the second portion of the spindle for establishing an axial cogging relationship with the second longitudinally disposed sequence of magnet segments.

The embodiments of the present disclosure thus advantageously overcome the problems in the art in a number of ways. One actuator portion can contribute to the stiffness of the other actuator portion, and vice versa. In addition, changing an axial pole configuration of the axial actuator portion also reduces the mass moment of inertia of its rotor, which results in a lower spring stiffness requirement for the tangential actuator portion. Furthermore, the embodiments advantageously provide an opportunity to reduce a non-linear spring characteristic of both tangential and axial actuator portions by specific pole and magnet angle relative to each other. Still further, magnet volume reduction and thus manufacturing cost price reduction can be achieved.

Still further advantages and benefits will become apparent to those of ordinary skill in the art upon reading and understanding the following detailed description.

The embodiments of the present disclosure may take form in various components and arrangements of components, and in various steps and arrangements of steps. Accordingly, the drawings are for purposes of illustrating the various embodiments and are not to be construed as limiting the embodiments. In the drawing figures, like reference numerals refer to like elements. In addition, it is to be noted that the figures may not be drawn to scale.

The embodiments of the present disclosure and the various features and advantageous details thereof are explained more fully with reference to the non-limiting examples that are described and/or illustrated in the drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the present disclosure. The examples used herein are intended merely to facilitate an understanding of ways in which the embodiments of the present may be practiced and to further enable those of skill in the art to practice the same. Accordingly, the examples herein should not be construed as limiting the scope of the embodiments of the present disclosure, which is defined solely by the appended claims and applicable law.

It is understood that the embodiments of the present disclosure are not limited to the particular methodology, protocols, devices, apparatus, materials, applications, etc., described herein, as these may vary. It is also to be understood that the terminology used herein is used for the purpose of describing particular embodiments only, and is not intended to be limiting in scope of the embodiments as claimed. It must be noted that as used herein and in the appended claims, the singular forms "a," "an," and "the" include plural reference unless the context clearly dictates otherwise.

Unless defined otherwise, all technical and scientific terms used herein have the same meanings as commonly understood by one of ordinary skill in the art to which the embodiments of the present disclosure belong. Preferred methods, devices, and materials are described, although any methods and materials similar or equivalent to those described herein can be used in the practice or testing of the embodiments.

Figure 4:
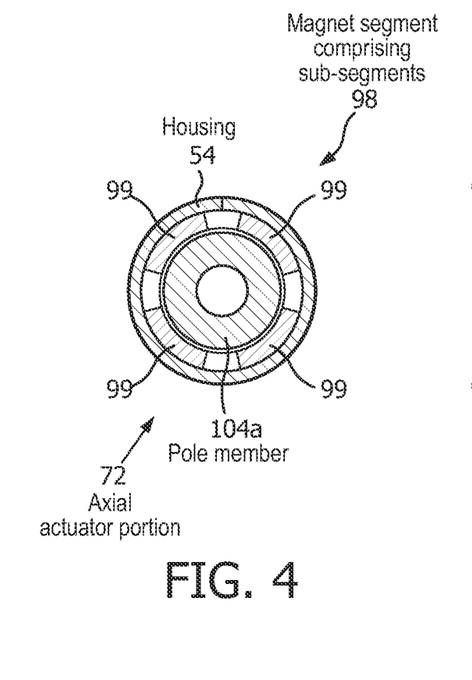
FIG. 4 is a cross-sectional view of one embodiment of a plurality of magnet sub-segments and a pole member of a magnet and pole assembly of the axial actuator portion of the actuator according to one embodiment the present disclosure.
Figure 5:
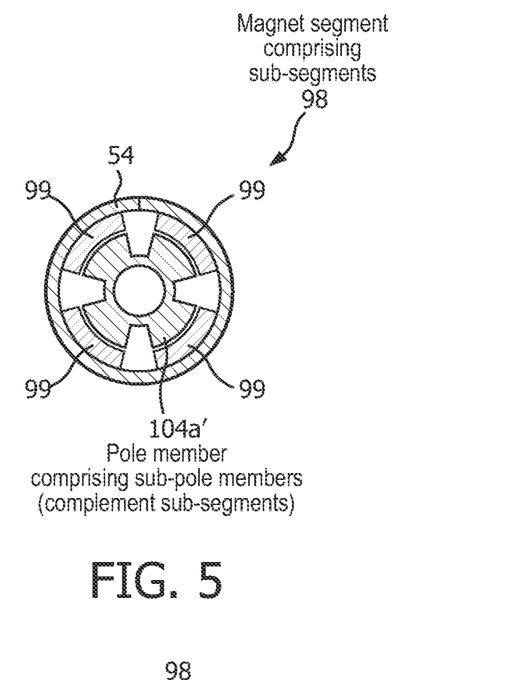
FIG. 5 is a cross-sectional view of another embodiment of a plurality of magnet sub-segments and a pole member of a magnet and pole assembly of the axial actuator portion of the actuator according to the present disclosure, wherein the pole member include a plurality of sub-pole members.
Figure 6:
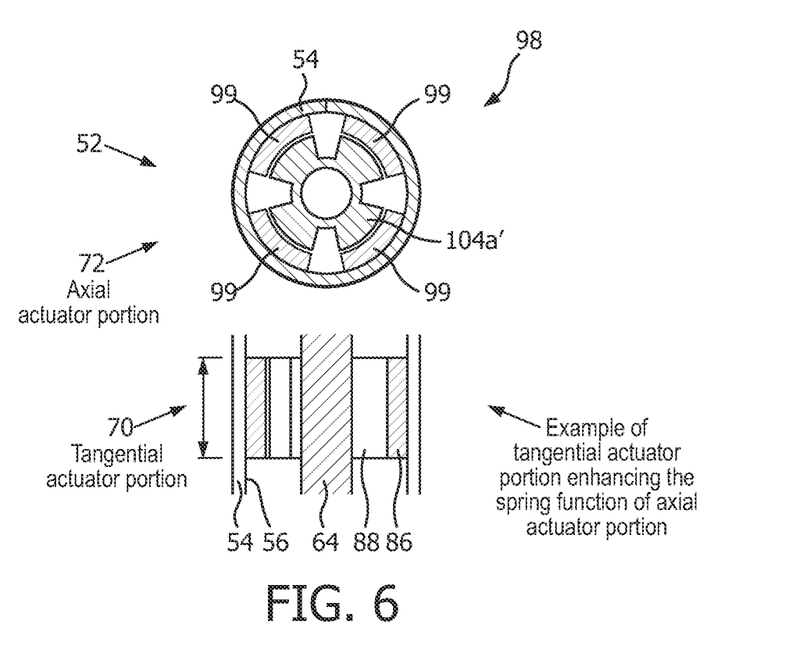
FIG. 6 is a cross-sectional view of another embodiment of the actuator according to the present disclosure in which the tangential actuator portion is configured for enhancing a spring function of the axial actuator portion, the axial actuator portion including a plurality of magnet sub-segments and a pole member that includes a plurality of sub-pole members.

According to one or more embodiments discussed herein, an axial magnet volume of a dual function actuator is reduced by introducing segments into the axial actuator (i.e., axial stator magnet segments), such as illustrated and to be discussed further herein with respect to FIGS. 4, 5 and 6. One advantage of segmenting the axial stator magnets is less magnet volume and lower stiffness on the axial actuator portion.

Figure 2:
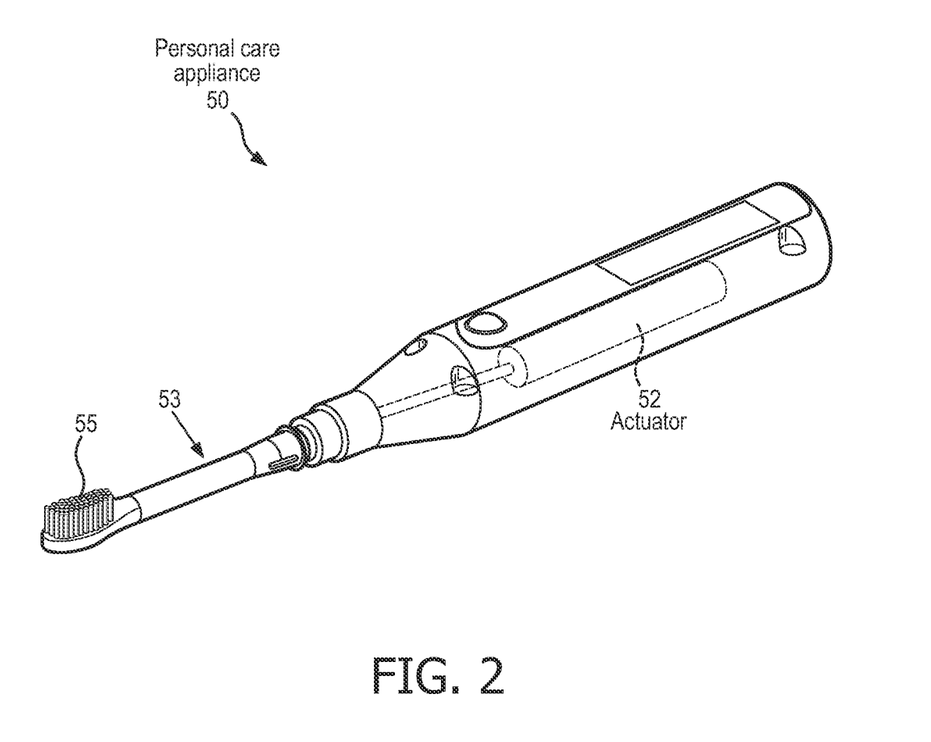
FIG. 2 is a perspective view of a personal care appliance that includes an actuator, i.e, a dual motion actuator, having a tangential actuator portion and an axial actuator portion according to an embodiment of the present disclosure.

Turning now to FIG. 2, there is shown a perspective view of a personal care appliance 50 that includes a drive system that includes an actuator 52 (i.e., a dual motion actuator) according to an embodiment of the present disclosure. In one embodiment, the personal care appliance 50 comprises a power toothbrush. The actuator 52 is generally disposed within a handle of the personal care appliance 50. The actuator 52 uses magnetic action to drive an output mounting shaft 53 on which is mounted a workpiece 55, for example, a brushhead for the power toothbrush.

Figure 3:
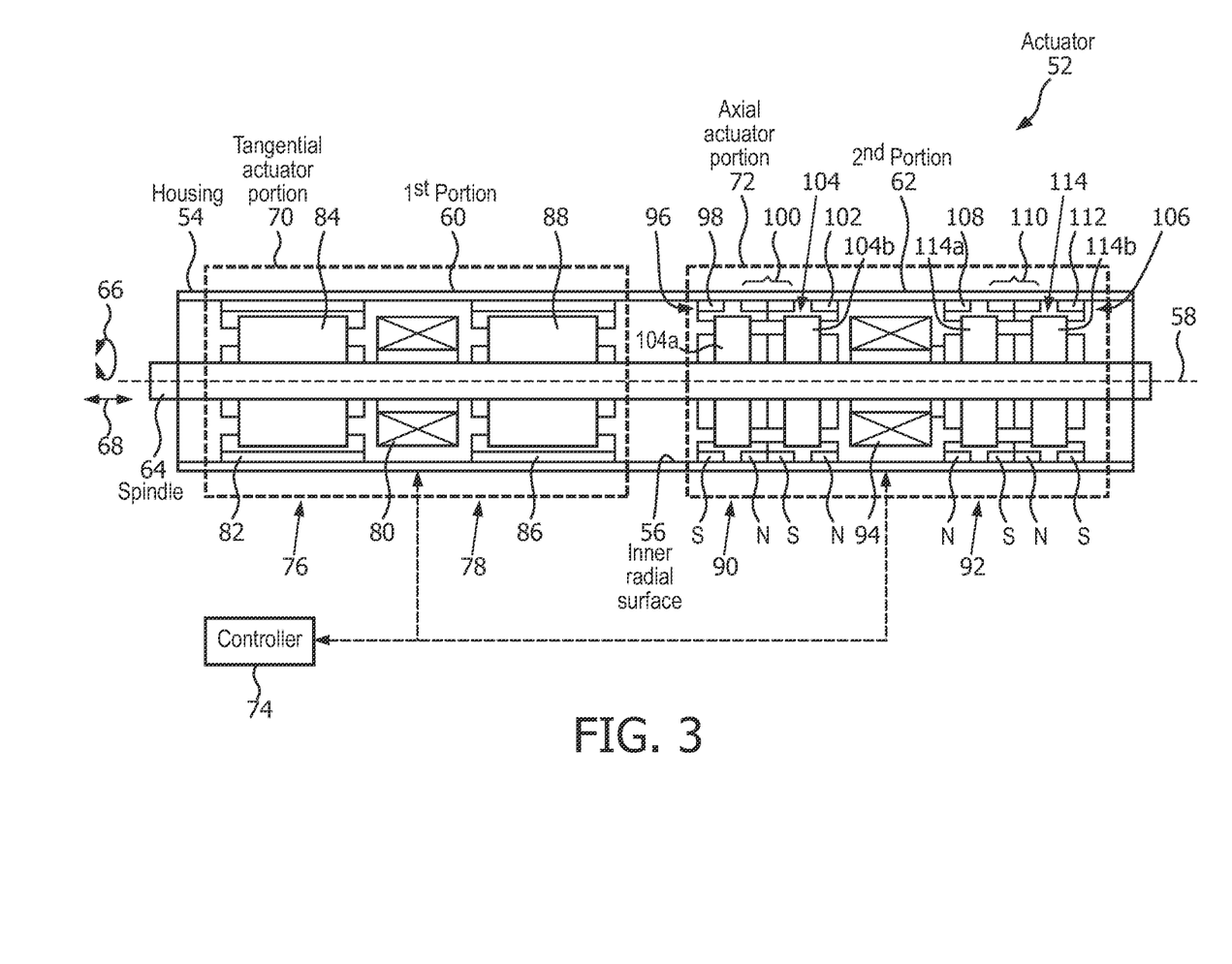
FIG. 3 is a schematic view of an actuator having a tangential actuator portion and an axial actuator portion according to an embodiment of the present disclosure.

With reference now to FIG. 3, there is shown a schematic view of the actuator 52 according to an embodiment of the present disclosure, in greater detail. Actuator 52 comprises a cylindrical housing 54 of magnetic material having an inner radial surface 56 and a principal axis 58 extending longitudinally along a length dimension thereof. The housing 54 also includes at least first and second portions, indicated by referenced numerals 60 and 62, respectively, along the length dimension thereof. The actuator further comprises a spindle 64 of magnetizable material extending longitudinally within the housing 54 along the principal axis 58 of the housing. The spindle also includes at least first and second portions corresponding with the at least first and second portions 60 and 62, respectively, of the housing 54. Spindle 64 is mechanically coupled, via bearings or other suitable means known in the art, with respect to the housing 54. As a result, spindle 64 is enabled for both a rotational motion 66 and an axial motion 68 of the spindle with respect to the housing 54.

Actuator 52 further comprises a tangential actuator portion 70 and an axial actuator portion 72. The tangential actuator portion 70 is coupled between the first portion 60 of the housing 54 and the corresponding first portion of the spindle 64, whereas the axial actuator portion 72 is coupled between the second portion 62 of the housing 54 and the corresponding second portion of the spindle 64.

With reference still to FIG. 3, actuator 52 further comprises a controller 74, wherein the controller includes any suitable microprocessor, microprocessors, controller, controllers, or other type of suitable control device known in the art. In particular, controller 74 is configured for providing at least one selected from the group consisting of (i) a rotation control signal to the tangential actuator portion 70, (ii) a translation control signal to the axial actuator portion 72, and (iii) any combination of both rotation and translation control signals, according to the particular requirements of a given actuator implementation. For example, the rotation and translation control signals can be configured to provide multiple different actuator motions and/or operational modes for the personal care appliance 50.

The tangential actuator portion 70 of actuator 52 according to one embodiment of the present disclosure is coupled between the first portion 60 of the housing 54 and the corresponding first portion of the spindle 64. The tangential actuator portion 70 comprises (i) a first permanent magnet and pole assembly 76, (ii) a second permanent magnet and pole assembly 78 and (iii) an electromagnetic coil 80 (or electromagnetic coil winding).

The first permanent magnet and pole assembly 76 of the tangential actuator portion 70 comprises (i)(a) a first sequence 82 of magnet segments spaced apart and having a first polarity order. The first polarity order can include, for example, a first N magnet segment, a free space, a second S magnet segment, a second free space, etc., until an $n_1^{th}$ S magnet segment, and $n_1^{th}$ free space, where "$n_1$" is an integer number. For example, the integer number $n_1$ can equal 5 (i.e., $n_1=5$) in one embodiment, further wherein the radial orientation comprises thirty-six (36) degrees between the centers of adjacent ones of the magnet segments. However, "$n_1$" can represent any reasonable number of magnet segments configured for a given tangential actuator portion implementation. For example, "$n_1$" could be equal to 4. In addition, each magnet segment of the first sequence 82 is longitudinally disposed along the inner radial surface 56 within the first portion 60 of the housing 54.

The first permanent magnet and pole assembly 76 of the tangential actuator portion 70 further comprises (i)(b) a first pole assembly 84 having a first set of pole members arranged in a first radial configuration disposed about the spindle 64 on the corresponding first portion of the spindle. The first set of pole members in the first radial configuration can include for example, a number of "$m_1$" poles, where "$m_1$" is an integer number. In one embodiment, the value of "$m_1$"="$n_1$" of the first sequence 82 of magnet segments.

In addition, a free end radial surface of each pole member of the first pole assembly 84 extends radially outward towards an inner radial surface of the first sequence 82 of magnet segments, proximate to, but separated by a gap from, the inner radial surface of the first sequence 82 of magnet segments. Still further, in one embodiment, the outer radial surface of each pole member complements an inner radial surface of an individual magnet segment.

The second permanent magnet and pole assembly 78 of the tangential actuator portion 70 is similar to that of the first permanent magnet and pole assembly 76 with the following differences. The second permanent magnet and pole assembly 78 comprises (ii)(a) a second sequence 86 of magnet segments spaced apart in a second radial orientation and having a second polarity order, opposite to the first polarity order. The second radial orientation and second polarity order can include, for example, a first S magnet segment, a free space, a second N magnet segment, a second free space, etc., until an $n_2^{th}$ N magnet segment, and $n_2^{th}$ free space, where "$n_2$" is an integer number. For example, the integer number $n_2$ can equal 5 (i.e., $n_2$=5) in one embodiment, further wherein the radial orientation comprises thirty-six (36) degrees between the centers of adjacent ones of the magnet segments. However, "$n_2$" can represent any reasonable number of magnet segments configured for a given actuator implementation. For example, "$n_2$" could be equal to 4 (i.e., $n_2$=4). In addition, each magnet segment of the second sequence 86 is longitudinally disposed along the inner radial surface 56 within the first portion 60 of the housing 54.

The second permanent magnet and pole assembly 78 of the tangential actuator portion 70 further comprises (ii)(b) a second pole assembly 88 having a second set of pole members arranged in a second radial configuration disposed about the spindle 64 on the first portion of the spindle. The second set of pole members in the second radial configuration can include for example, a number of "$m_2$" poles, where "$m_2$" is an integer number. In one embodiment, the value of "$m_2$"="$n_2$" of the second sequence 86 of magnet segments.

In addition, a free end radial surface of each pole member of the second pole assembly 88 extends radially outward towards an inner radial surface of the second sequence 86 of magnet segments, proximate to, but separated by a gap from, the inner radial surface of the second sequence 86 of magnet segments. Still further, in one embodiment, the outer radial surface of each pole member complements an inner radial surface of an individual magnet segment.

The tangential actuator portion 70 further comprises the electromagnetic coil 80 (or electromagnetic coil winding). The electromagnetic coil 80 is disposed about and coupled to the spindle 64 in-between the first and second magnet and pole assemblies, 76 and 78, respectively. Responsive to a rotation control signal applied to the electromagnetic coil 80 from the controller 74, the tangential actuator portion 70 rotationally displaces the spindle 64 with respect to the housing 54 about the principal axis 58, and thus imparting a desired rotational motion 66 to spindle 64. The desired rotational motion can comprise, for example, rotational motion having a peak-to-peak amplitude with a range of 9-11°, or other range, as appropriate for a given actuator implementation. As indicated herein, the rotation and translation control signals can be configured to provide multiple different actuator motions and/or operational modes for the personal care appliance 50. For example, the controller will drive the actuator(s) to near-resonance, further according to desired operating characteristics of a given personal care appliance implementation.

With reference still to FIG. 3, the axial actuator portion 72 is coupled between the second portion 62 of the housing 54 and the corresponding second portion of the spindle 64. The axial actuator portion 72 comprises (i) a third permanent magnet and pole assembly 90, (ii) a fourth permanent magnet and pole assembly 92 and (iii) an electromagnetic coil 94 (or electromagnetic coil winding).

The third permanent magnet and pole assembly 90 of the axial actuator portion 72 comprises (i)(a) a third sequence 96 of magnet segments (as indicated by reference numerals 98, 100 and 102) spaced apart in a first longitudinal orientation and having a third polarity order. The first longitudinal orientation and third polarity order can include, for example, a magnet segment 98, a free space, a second magnet segment 100, . . . , an $n^{th}$ free space, and $n^{th}$ magnet segment 102, where "n" is an integer number. In one embodiment the integer number n is equal to 3 (i.e., n=3), further wherein the longitudinal orientation comprises a predetermined spacing between adjacent ones of the magnet segments. However, "n" can represent any reasonable number of magnet segments configured for a given axial actuator portion implementation. In one embodiment, the intermediate magnet segments, such as segment 100, can comprise an individual N-S (or S-N) grouped magnet segment, as will be discussed further herein.

Each segment (e.g., segments 98, 100, 102) of the third sequence 96 of magnet segments is circumferentially disposed about the inner radial surface 56 within the second portion 62 of the housing 54 and at a respective longitudinal position along the length dimension of the housing. In other words, each segment is in the form of a ring about an inner periphery of the housing at a respective position along the length dimension of the housing. In one embodiment, segment 98 comprises an S-polarity magnet segment, segment 100 comprises an individual N-S grouped magnet segment, and segment 102 comprises an N-polarity magnet segment.

With reference now to FIG. 4, there is shown a cross-sectional view of one embodiment of a plurality of magnet sub-segments and a pole member of a magnet and pole assembly of the axial actuator portion 72 of the actuator 52 according to one embodiment of the present disclosure. As illustrated in FIG. 4, segment 98 further comprises a ring of sub-segments 99 of a given magnetic polarity, for example, S-polarity. The ring of sub-segments 99 are individual spaced apart sub-segments that collectively form segment 98 disposed about the inner radial surface 56. Segment 102 (FIG. 3) is similar to segment 98 and also comprises sub-segments that collectively form segment 98. With respect to segment 100 (FIG. 3), it also includes sub-segments similar to the sub-segments of the segments 98 and 102; however, each sub-segment of segment 100 comprises an individual N-S grouped magnet sub-segment. In one embodiment, an N-polarity portion of each individual N-S grouped magnet sub-segment of segment 100 is located to the right side of segment 98 (S-polarity), while an S-polarity portion of each individual N-S grouped magnet sub-segment of segment 100 is located to the left side of segment 102 (N-polarity).

In one embodiment, the number of sub-segments of each respective segment 98, 100 and 102 comprises four. The four sub-segments of each respective segment 98, 100 and 104 are equally spaced apart from one another about a given circumference, i.e., about the inner radial surface 56 of housing 54. In addition, the radial and axial dimensions of each respective sub-segment is determined according to the particular requirements of the given axial actuator portion 72. For example, each of the sub-segments can extend over radial distance of approximately 60° and the corresponding spacing between adjacent sub-segments can extend over a radial distance of approximately 30° for each respective segment 98, 100 and 102, for example, as shown in FIG. 4 with respect to sub-segments 99.

With reference again to FIG. 3, the third permanent magnet and pole assembly 90 of the axial actuator portion 72 further comprises (i)(b) a third pole assembly 104 having a least one pole member disposed about the spindle 64 on the second portion of the spindle. As illustrated in FIG. 3, the third pole assembly 104 includes a first and second pole member, indicated by reference numerals 104a and 104b, respectively. In addition, the radial and axial dimensions of each respective pole member is determined according to the particular requirements of the given axial actuator portion 72. In one embodiment, each of the first and second pole members comprises a respective solid unitary pole member. In addition, each of the first and second pole members is longitudinally positioned between a given set of first and second magnet segments, corresponding to a respective longitudinal cogging position. For example, the first pole member 104a is positioned between segments 98 and 100, and the second pole member 104b is positioned between segments 100 and 102. As indicated above, segment 100 comprises an individual N-S grouped magnet segment. The individual N-S grouped magnet segment 100 is thus shared during operation of the axial actuator portion, i.e., alternating actuation between the first pole member 104a and the second pole member 104b.

With reference still to FIG. 3, the fourth permanent magnet and pole assembly 92 of the axial actuator portion 72 is similar to that of the third permanent magnet and pole assembly 90 with the following differences. The fourth permanent magnet and pole assembly 92 comprises (ii)(a) a fourth sequence 106 of magnet segments (as indicated by reference numerals 108, 110 and 112) spaced apart in a second longitudinal orientation and having a fourth polarity order, opposite to the third polarity order. The second longitudinal orientation and fourth polarity order can include, for example, a magnet segment 108, a free space, a second magnet segment 110, . . . , an $n_2^{th}$ free space, and $n_2^{th}$ magnet segment 112, where "$n_2$" is an integer number. As shown in FIG. 3, in one embodiment the integer number $n_2$ is equal to 3 (i.e., $n_2$=3), further wherein the longitudinal orientation comprises a predetermined spacing between adjacent ones of the magnet segments. However, "$n_2$" can represent any reasonable number of magnet segments configured for a given axial actuator portion implementation. In one embodiment, the intermediate magnet segments, such as segment 110, can comprise an individual N-S (or S-N) grouped magnet segment, as will be discussed further herein.

Each segment (e.g., segments 108, 110, 112) of the fourth sequence 106 of magnet segments is circumferentially disposed about the inner radial surface 56 within the second portion 62 of the housing 54. In other words, each segment is in the form of a ring about an inner periphery of the housing at a respective position along the length dimension of the housing. In one embodiment, segment 108 comprises an N-polarity magnet segment, segment 102 comprises an individual N-S grouped magnet segment, and segment 112 comprises an S-polarity magnet segment.

In addition, similarly to that illustrated with reference to FIG. 4 and discussed herein above, each of the segments 108, 110 and 112 further comprises a ring of sub-segments of a respective magnetic polarity. The sub-segments are individual spaced apart sub-segments that collectively form a respective segment disposed about the inner radial surface 56 of housing 54. As illustrated in FIG. 3, an S-polarity portion of each individual N-S grouped magnet sub-segment of segment 110 is located to the right side of segment 108, while an N-polarity portion of each individual N-S grouped magnet sub-segment of segment 110 is located to the left side of segment 112.

In one embodiment, the number of sub-segments of each respective segment 108, 110 and 112 comprises four. The four sub-segments of each respective segment 108, 110 and 112 are equally spaced apart from one another about a given circumference, i.e., about the inner radial surface 56 of housing 54. In addition, the radial and axial dimensions of each respective sub-segment is determined according to the particular requirements of the given axial actuator portion 72. For example, each of the sub-segments can extend over radial distance of approximately 60° and the corresponding spacing between adjacent sub-segments can extend over a radial distance of approximately 30° for each respective segment 108, 110 and 112, for example, similarly as shown in FIG. 4 with respect to sub-segments 99.

The fourth permanent magnet and pole assembly 92 of the axial actuator portion 72 further comprises (ii)(b) a fourth pole assembly 114 having a least one pole member disposed about the spindle 64 on the second portion of the spindle. As illustrated in FIG. 3, the fourth pole assembly 114 includes a first and second pole member, indicated by reference numerals 114a and 114b, respectively. In addition, the radial and axial dimensions of each respective pole member is determined according to the particular requirements of the given axial actuator portion 72. In one embodiment, each of the first and second pole members comprises a respective solid unitary pole member. In addition, each of the first and second pole members is longitudinally positioned between a given set of first and second magnet segments, corresponding to a respective longitudinal cogging position. For example, the first pole member 114a is positioned between segments 108 and 110, and the second pole member 114b is positioned between segments 110 and 112. As indicated above, segment 110 comprises an individual N-S grouped magnet segment. The individual N-S grouped magnet segment 110 is thus shared during operation of the axial actuator portion, i.e., alternating actuation between the first pole member 114a and the second pole member 114b.

In addition to the above, the free end radial surfaces of each pole member (e.g., 104a, 104b of the third pole assembly 104 extends radially outward towards an inner radial surface of the third sequence 96 of magnet segments, proximate to, but separated by a gap from, the inner radial surface of the third sequence 96 of magnet segments. Furthermore, the free end radial surfaces of each pole member (e.g., 114a, 114b) of the fourth pole assembly 114 extends radially outward towards an inner radial surface of the fourth sequence 106 of magnet segments, proximate to, but separated by a gap from, the inner radial surface of the fourth sequence 106 of magnet segments.

With reference still to FIG. 3, the axial actuator portion 72 further comprises the electromagnetic coil 94 (or electromagnetic coil winding). The electromagnetic coil 94 is disposed about and coupled to the spindle 64 in-between the third and fourth magnet and pole assemblies, 90 and 92, respectively. Responsive to a translation control signal (or axial control signal) applied to the electromagnetic coil 94 from the controller 74, the axial actuator portion 72 axially displaces the spindle 64 with respect to the housing 54 along the principal axis 58, and thus imparting a desired axial motion 68 to spindle 64. The desired axial motion can comprise, for example, axial motion having a peak-to-peak amplitude up to 1 mm, or other range, as appropriate for a given actuator implementation. As indicated herein, the rotation and translation control signals can be configured to provide multiple different actuator motions and/or operational modes for the personal care appliance 50 (FIG. 2).

With respect to each sub-segment of segment 100 that comprises an individual N-S grouped magnet sub-segment and with respect to each sub-segment of segment 110 that also comprises an individual N-S grouped magnet sub-segment, each sub-segment comprises a single magnet segment having a N-S or S-N magnetization pattern, respectively. As discussed herein, the magnets are combined pair wise (i.e., N-S or S-N). In this configuration, each N-S pair (or S-N pair) is made from one segment, and the N-S (S-N) magnetization pattern is created by a suitable magnetization process. Magnetization of the segments (e.g., the segments can comprise iron stators) can be accomplished after being mounted within the actuator housing. A boundary will be defined between N and S portions of each segment (or stator) via the magnetization process.

With reference now to FIG. 5, there is shown a cross-sectional view of a plurality of magnet sub-segments and a pole member that includes a plurality of sub-pole members. As discussed herein above, with reference to FIG. 4, the pole assembly 104 of the magnet and pole assembly 90 can include a solid disc pole member 104a as shown in FIG. 4. However, for a given actuator implementation, the solid disc in the embodiment of FIG. 4 could retain too high a spring constant for the given actuator implementation, and so the solid disc of the axial actuator portion is advantageously segmented as shown in segmented disc pole member 104a' of FIG. 5.

In particular, the pole member is segmented into sub-pole members, along with segmenting of corresponding axial stator magnets, to reduce its corresponding spring constant. The rotor (i.e., the segmented disc 104a' or core member of the axial actuator portion), along with other pole members coupled to the shaft or spindle, will also oscillate tangentially as driven by the tangential actuator portion 70 of the dual motion actuator 52. Segmenting of the disc, in addition to segmenting the axial magnets, as discussed herein, advantageously creates additional tangential stiffness due to a preferred position of the segmented core towards the magnet segments, for example, as shown in FIG. 5. Furthermore, since tangential stiffness is advantageously increased via the embodiment of FIG. 5 and the axial actuator portion, less magnet volume will be needed for the tangential actuator portion.

With reference still to FIG. 5, the segmented disc 104a' (i.e., core) of the axial actuator portion introduces a lower moving mass and mass moment of inertia, which enables once more a lower spring constant, both tangential, as well as, axial. This reduces therefore once more the total magnet volume for the dual motion actuator.

With reference now to FIG. 6, there is shown a cross-sectional view of another embodiment of the dual motion actuator 52 according to the present disclosure in which the tangential actuator portion 70 is configured for enhancing a spring function of the axial actuator portion 72, the axial actuator portion including a plurality of magnet sub-segments and a pole member that includes a plurality of sub-pole members. The embodiment of FIG. 6 provides for a reverse effect. That is, the tangential core, e.g., indicated in part by reference numeral 88 in FIG. 6, is tuned to add axial stiffness to the dual motion actuator 52. Tuning of the tangential core advantageously provides for a further reduction of axial magnet volume, for example, as shown in FIG. 6. In addition, the respective rotor and stator of the tangential actuator portion 70 and the axial actuator portion 72 correspond along their respective radial edges, for better strength and spring constant.

Accordingly, the embodiments of the present disclosure advantageously provide overall results of an improved optimum for two actuator portions of a dual motion actuator in one housing, and lower manufacturing cost. In one embodiment, changing of the axial pole and magnet shapes of the axial system is deliberately configured to beneficially affect the tangential system, i.e., the tangential stiffness of the tangential actuator portion of the dual motion actuator. In another embodiment, the tangential pole and magnet configuration of the tangential actuator portion is also tuned to provide additional axial stiffness to the axial system, i.e., the axial stiffness of the axial actuator portion of the dual motion actuator.

Although only a few exemplary embodiments have been described in detail above, those skilled in the art will readily appreciate that many modifications are possible without materially departing from the novel teachings and advantages of the embodiments of the present disclosure. For example, the actuator housing can be a shape other than cylindrical. In addition, the embodiments of the present disclosure can be advantageously used in electrical tooth brushes, oral hygiene devices, teeth polishing devices, or other type of personal care appliance with dual motions. Accordingly, all such modifications are intended to be included within the scope of the embodiments of the present disclosure as defined in the following claims. In the claims, means-plus-function clauses are intended to cover the structures described herein as performing the recited function and not only structural equivalents, but also equivalent structures.

In addition, any reference signs placed in parentheses in one or more claims shall not be construed as limiting the claims. The word "comprising" and "comprises," and the like, does not exclude the presence of elements or steps other than those listed in any claim or the specification as a whole. The singular reference of an element does not exclude the plural references of such elements and vice-versa. One or more of the embodiments may be implemented by means of hardware comprising several distinct elements, and/or by means of a suitably programmed computer. In a device claim enumerating several means, several of these means may be embodied by one and the same item of hardware. The mere fact that certain measures are recited in mutually different dependent claims does not indicate that a combination of these measures cannot be used to an advantage.

The invention claimed is:

1. An actuator for a personal care appliance comprising:
   (a) a housing of magnetic material having an inner surface and a principal axis extending along a length dimension thereof, the housing further including at least first and second portions along the length dimension thereof,
   (b) a spindle of magnetizable material extending longitudinally within the housing along the principal axis, the spindle further including at least first and second portions corresponding with the at least first and second portions of the housing, respectively;
   (c) a tangential actuator portion coupled between the first portion of the housing and the first portion of the spindle, wherein the tangential actuator portion comprises (i) a first magnet and pole assembly, (ii) a second magnet and pole assembly (iii) a space arranged between the first magnet and pole assembly and the second magnet and pole assembly, and (iv) an electromagnetic coil disposed about and coupled to the spindle, the electromagnetic coil further disposed in-between the first and second magnet and pole assemblies and within the space, wherein responsive to a rotation control signal applied to the electromagnetic coil, the tangential actuator portion rotationally displaces the spindle with respect to the housing about the principal axis; and
   (d) an axial actuator portion coupled between the second portion of the housing and the second portion of the spindle, wherein the axial actuator portion comprises (i) a third magnet and pole assembly, (ii) a fourth magnet and pole assembly, and (iii) a second electromagnetic coil disposed about and coupled to the spindle in-between the third and fourth magnet and pole assemblies, wherein responsive to a translation control signal applied to the second electromagnetic coil, the axial actuator portion axially displaces the spindle with respect to the housing along the principal axis, wherein the first and second magnet and pole assemblies define a tangential spring function of the tangential actuator portion, and the third and fourth magnet and pole assemblies define an axial spring function of the axial actuator portion, and wherein the tangential actuator portion and the axial actuator portion further comprise at least one of (i) the first and second magnet and pole assemblies of the tangential actuator portion configured to enhance the axial spring function of the axial actuator portion, and (ii) third and fourth magnet and pole assemblies of the axial actuator portion configured to enhance the tangential spring function of the tangential actuator portion,
   wherein the third magnet and pole assembly comprises a first segment of a first sequence of magnets, the first sequence of magnets being spaced apart according to a first longitudinal spacing pattern, the first segment of the first sequence of magnets being circumferentially disposed about the inner surface within the second portion of the housing, wherein the first segment of the first sequence of magnets comprises at least two sub-segments spaced apart from one another by a given radial spacing about the circumference of the inner surface.

2. The actuator of claim 1, further wherein the first and second magnet and pole assemblies of the tangential actuator portion are configured to increase a stiffness in the axial spring function of the axial actuator portion, and wherein the third and fourth magnet and pole assemblies of the axial actuator portion are configured to increase a stiffness in the tangential spring function of the tangential actuator portion.

3. The actuator of claim 1, wherein a complement of sub-pole members and magnet sub-segments of the axial actuator portion produces a spring function that enhances the tangential spring function of the tangential actuator portion of the actuator.

4. The actuator of claim 1, wherein the third magnet and pole assembly comprises (i)(a) the first sequence of magnet segments is spaced apart according to the first longitudinal spacing pattern and having a first polarity order, each segment of the first sequence of magnet segments being circumferentially disposed about the inner surface within the second portion of the housing, wherein the first segment of the first sequence of magnet segments comprises at least two sub-segments of a same polarity spaced apart from one another by a given radial spacing about a respective given circumference of the inner surface, and (i)(b) a third pole assembly having a least one pole member disposed about and on the second portion of the spindle.

5. The actuator of claim 1, wherein the first segment of the first sequence of magnet segments further comprises at least two segments, wherein (i) a first one of the at least two segments comprises sub-segments of a first polarity spaced apart about a respective given circumference of the inner surface and (ii) a second one of the at least two segments comprises sub-segments of a second polarity, opposite the first polarity, spaced apart about a respective given circumference of the inner surface.

6. The actuator of claim 5, further wherein (i) the first one of the at least two segments of the first sequence of magnet segments and (ii) the second one of the at least two segments of the first sequence of magnet segments (iii) comprise neighboring segments.

7. The actuator of claim 5, wherein the at least one pole member of the third pole assembly further comprises at least two sub-pole members arranged in a first radial configuration disposed about the spindle, wherein the first radial configuration comprises the at least two sub-pole members being configured to complement the at least two sub-segments of the at least one segment of the first sequence of magnet segments, and wherein sub-pole members complement sub-segments by (i) a free-end radial surface of each sub-pole member extending radially outward towards an inner radial surface of a corresponding sub-segment proximate to, but separated by a gap from, the inner radial surface of a corresponding sub-segment, and (ii) a free-end radial dimension of each sub-pole member being approximately equal to an inner radial dimension of a corresponding sub-segment.

8. The actuator of claim 5, wherein the fourth magnet and pole assembly comprises (ii)(a) a second sequence of magnet segments spaced apart according to a second longitudinal spacing pattern and having a second polarity order, opposite to the first polarity order, each segment of the second sequence of magnet segments being circumferentially disposed about the inner surface within the second portion of the housing, and (ii)(b) a fourth pole assembly having a least one pole member disposed about and on the second portion of the spindle.

9. The actuator of claim 8, wherein at least one segment of the second sequence of magnet segments comprises at least two sub-segments of a same polarity spaced apart from one another by a given radial spacing about a respective given circumference of the inner surface.

10. The actuator of claim 9, wherein the at least one segment of the second sequence of magnet segments further comprises at least two segments, wherein (i) a first one of the at least two segments comprises sub-segments of a first polarity spaced apart about a respective given circumference of the inner surface and (ii) a second one of the at least two segments comprises sub-segments of a second polarity, opposite the first polarity, spaced apart about a respective given circumference of the inner surface.

11. The actuator of claim 10, further wherein (i) the first one of the at least two segments of the second sequence of magnet segments and (ii) the second one of the at least two segments of the second sequence of magnet segments (iii) comprise neighboring segments.

12. The actuator of claim 9, wherein the at least one pole member of the fourth pole assembly further comprises at least two sub-pole members arranged in a second radial configuration disposed about the spindle, wherein the second radial configuration comprises the at least two sub-pole members being configured to complement the at least two sub-segments of the at least one segment of the second sequence of magnet segments, and wherein sub-pole members complement sub-segments by (i) a free-end radial surface of each sub-pole member extending radially outward towards an inner radial surface of a corresponding sub-segment proximate to, but separated by a gap from, the inner radial surface of a corresponding sub-segment, and (ii) a free-end radial dimension of each sub-pole member being approximately equal to an inner radial dimension of a corresponding sub-segment.

13. The actuator of claim 1, further comprising:
(a) a controller for providing at least one selected from the group consisting of the rotation control signal, the translation control signal, and any combination of both rotation and translation control signals.

14. A personal care appliance, comprising the actuator according to claim 1, wherein the personal care appliance comprises one selected from the group consisting of an electric toothbrush, an oral hygiene device, a tooth polishing device, and any combination thereof.

15. An actuator for a personal care appliance comprising:
(a) a housing of magnetic material having an inner radial surface and a principal axis extending along a length dimension thereof, the housing further including at least first and second portions along the length dimension thereof;
(b) a spindle of magnetizable material extending longitudinally within the housing along the principal axis, the spindle further including at least first and second portions corresponding with the at least first and second portions of the housing, respectively;
(c) a tangential actuator portion coupled between the first portion of the housing and the first portion of the spindle, wherein the tangential actuator portion comprises (i) a first magnet and pole assembly, (ii) a second magnet and pole assembly, (iii) a space arranged between the first magnet and pole assembly and the second magnet and pole assembly, and (iv) an electromagnetic coil disposed about and coupled to the spindle, the electromagnetic coil further disposed in-between the first and second magnet and pole assemblies and within the space, wherein responsive to a rotation control signal applied to the electromagnetic coil, the tangential actuator portion rotationally displaces the spindle with respect to the housing about the principal axis;
(d) an axial actuator portion coupled between the second portion of the housing and the second portion of the spindle, wherein the axial actuator portion comprises (i) a third magnet and pole assembly, (ii) a fourth magnet and pole assembly, and (iii) a second electromagnetic coil disposed about and coupled to the spindle in-between the third and fourth magnet and pole assemblies, wherein responsive to a translation control signal applied to the second electromagnetic coil, the axial actuator portion axially displaces the spindle with respect to the housing along the principal axis; and
(e) a controller for providing at least one selected from the group consisting of the rotation control signal, the translation control signal, and any combination of both rotation and translation control signals,
wherein the first and second magnet and pole assemblies define a tangential spring function of the tangential actuator portion, and the third and fourth magnet and pole assemblies define an axial spring function of the axial actuator portion, and
wherein the tangential actuator portion and the axial actuator portion further comprises at least one of (i) the first and second magnet and pole assemblies of the tangential actuator portion configured to enhance the axial spring function of the axial actuator portion, and (ii) third and fourth magnet and pole assemblies of the of the axial actuator portion configured to enhance the tangential spring function of the tangential actuator portion,
further wherein the third magnet and pole assembly comprises (i)(a) a first sequence of magnet segments spaced apart according to a first longitudinal spacing pattern and having a first polarity order, each segment of the first sequence of magnet segments being circumferentially disposed about the inner radial surface within the second portion of the housing, wherein at least one segment of the first sequence of magnet segments comprises at least two sub-segments of a same polarity spaced apart from one another by a given radial spacing about a respective given circumference of the inner radial surface, and (i)(b) a third pole assembly having a least one pole member disposed about and on the second portion of the spindle, and
further wherein the fourth magnet and pole assembly comprises (ii)(a) a second sequence of magnet segments spaced apart according to a second longitudinal spacing pattern, opposite to the first polarity order, each segment of the second sequence of magnet segments being circumferentially disposed about the inner radial surface within the second portion of the housing, and (ii)(b) a fourth pole assembly having a least one pole member disposed about and on the second portion of the spindle.

* * * * *